United States Patent [19]  [11]  4,453,975
Takematsu et al.  [45]  Jun. 12, 1984

[54] HERBICIDAL COMPOSITION

[75] Inventors: Tetsuo Takematsu, Utsunomiya; Akinori Suzuki, Chiba; Kazuya Toda, Ichikawa, all of Japan

[73] Assignee: Yashima Chemical Industrial Co., Ltd., Tokyo, Japan

[21] Appl. No.: 351,926

[22] Filed: Feb. 24, 1982

[30] Foreign Application Priority Data

Mar. 3, 1981 [JP] Japan ................................. 56/29319

[51] Int. Cl.³ ..................... A01N 37/22; C07C 103/76
[52] U.S. Cl. ....................................... 71/118; 564/182
[58] Field of Search ........................... 71/118; 564/182

[56] References Cited

U.S. PATENT DOCUMENTS 3,022,302 2/1962 Martensson et al. ............... 564/182

FOREIGN PATENT DOCUMENTS 55-167203 12/1980 Japan .
55-162757 12/1980 Japan .
56-108752 8/1981 Japan .
56-110655 9/1981 Japan .

OTHER PUBLICATIONS

Chemical Abstracts, vol. 85, (1976), 62766t.
Chemical Abstracts, vol. 48, (1954), 8193b.
Jpn. Kokai 80, 149,239, Chem. Abst. vol. 94, 156574s.

Primary Examiner—Catherine W. Mills
Attorney, Agent, or Firm—Wenderoth, Lind & Ponack

[57] ABSTRACT

A herbicidal composition containing as an active ingredient a compound of the formula

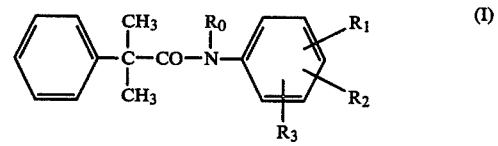

wherein $R_0$ represents a hydrogen atom or a lower alkyl group, and $R_1$, $R_2$ and $R_3$ each represent a hydrogen or halogen atom, or a lower alkyl, lower alkoxy or lower alkenyloxy group, which is especially useful for application to aquatic rice paddies, and novel compounds of formula (I) wherein $R_0$, $R_1$, $R_2$ and $R_3$ have the same meanings as defined above, provided that $R_1$, $R_2$ and $R_3$ do not represent hydrogen atom at the same time.

15 Claims, No Drawings

HERBICIDAL COMPOSITION

This invention relates to a novel herbicidal composition. More specifically, it pertains to a herbicidal composition containing a certain α,α-dimethylphenylacetanilide compound as an active ingredient, a method for controlling weeds in agricultural crops, especially rice (a gramineous plant), by using the aforesaid compound, and to some novel α,α-dimethylphenylacetanilide compounds.

Many phenylacetanilide derivatives have been known heretofore. For example, Chemical Abstracts (I), Vol. 85 (1976), 62766t summarizes a study on the phytotoxic activity of a group of phenylacetanilide derivatives having the α-carbon atom mono-substituted by a methyl group, i.e. hydratropic acid anilides. Chemical Abstracts, Vol. 48 (1954), 8193b states that α,α-dimethylphenylacetanilide is produced from isopropylphenyl acetophenone oxime.

However, no report has been made so far on the biological activity of phenylacetanilide derivatives having the α-carbon atom substituted with a methyl group.

We have synthesized α-α-dimethylphenylacetanilide and many of its derivatives. Consequently, we have now found that α,α-dimethylphenylacetanilide compounds of the formula

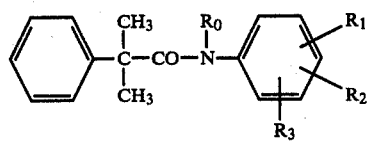
(I)

wherein $R_0$ represents a hydrogen atom or a lower alkyl group, and each of $R_1$, $R_2$ and $R_3$ represents a hydrogen or halogen atom, or a lower alkyl, lower alkoxy or lower alkenyloxy group, exhibit excellent selective biological activities on plants, and particularly when used as herbicides for application to rice paddies, do not cause any substantial phytotoxicity to useful crops of a rice paddy and exhibit strong herbicidal activity and growth-inhibiting activity against competing weeds such as barnyard grass (*Echinocholoa crus-galli* Beaux.), umbrella plant (*Cyperus difformis* L.) and water nutgrass (*Cyerus serotinus* Rottb.).

Thus, according to this invention, there is provided a herbicidal composition comprising a herbicidally effective amount of a compound of the formula

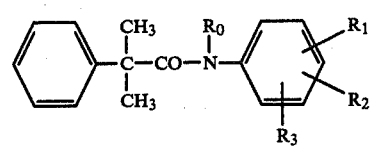
(I)

wherein $R_0$, $R_1$, $R_2$ and $R_3$ are as defined above, as an active ingredient and an inert liquid or solid carrier or diluent.

The herbicidal composition provided by this invention, as described above, has excellent inter-genus selective activity on gramineous plants, and while they cause substantially no phytotoxicity to rice, they have strong activity against barnyard grass which is a plant of the family Gramineae but belongs to a different genus from rice. In addition, the herbicidal composition of this invention exhibits excellent herbicidal activity and growth-inhibiting activity against weeds of the family Cyperaceae such as water nutgrass and umbrella plant.

Accordingly, the herbicidal composition of this invention contributes greatly to the advance of agriculture as a herbicide for application to rice paddies.

The term "lower", as used in the present specification and the appended claims, means that a group or compound qualified by this term has not more than 6, preferably not more than 4, carbon atoms.

The lower alkyl group in formula (I) may be linear or branched, and includes, for example, methyl, ethyl, propyl, isopropyl, butyl, isobutyl, sec-butyl, tert-butyl, and pentyl. The lower alkoxy group is a lower alkyloxy group in which the lower alkyl moiety is as defined above, and includes, for example, methoxy, ethoxy, propoxy, isopropoxy and butoxy. Alkoxy groups having 1 to 3 carbon atoms are preferred. The lower alkenyloxy group is preferably an allyloxy group.

The halogen atom includes fluorine, chlorine, bromine and iodine. Fluorine and chlorine are preferred.

Preferably, the substituent $R_0$ is a hydrogen atom or a methyl group.

As regards the substituents $R_1$, $R_2$ and $R_3$ on the benzene ring, it is preferred that one or two of these substituents be a hydrogen, chlorine or fluorine atom, an alkyl group with 1 to 4 carbon atoms or an alkoxy group with 1 to 3 carbon atoms, and the remainder be a hydrogen atom.

Of the compounds of formula (I), a class of preferred compounds are those represented by the following formula

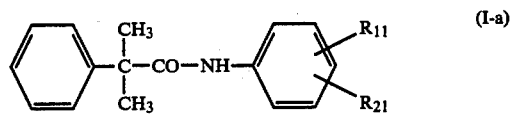
(I-a)

wherein $R_{11}$ and $R_{21}$ each represent a hydrogen atom or a methyl, ethyl, propyl, isopropyl or methoxy group, provided that $R_{11}$ and $R_{21}$ do not at the same time represent a hydrogen atom.

A class of more preferred compounds of formula (I-a) are those represented by the following formula

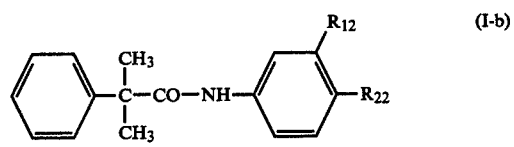
(I-b)

wherein $R_{12}$ and $R_{22}$ each represent a hydrogen atom, or a methyl, ethyl, propyl or isopropyl group, provided that $R_{12}$ and $R_{22}$ do not simultaneously represent a hydrogen atom.

As will be described in detail hereinbelow, the compounds of formula (I) provided by this invention have superior selective herbicidal activity. From the viewpoint of herbicidal activity, most preferred among the compounds of formula (I) are those of the following formulae

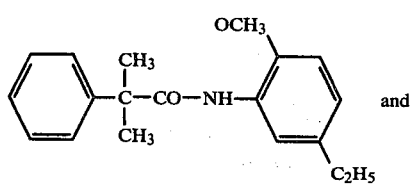 (I-c)

and

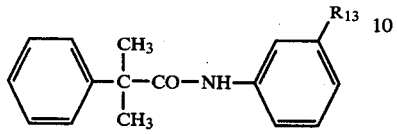

wherein R₁₃ represents a methyl, ethyl, propyl or isopropyl group.

The compounds of formula (I) used as the active ingredient in the herbicidal composition of this invention, except those of formula (I) in which $R_0$ represents a hydrogen atom and $R_1$, $R_2$ and $R_3$ are all hydrogen atoms, are considered to be novel compounds not described in the prior literature.

Thus, according to another aspect of this invention, there is provided a compound of the formula

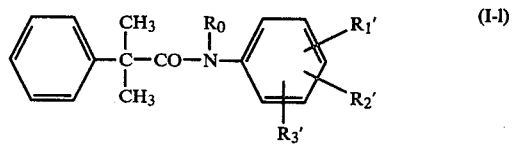 (I-1)

wherein $R_0$ represents a hydrogen atom or a lower alkyl group, and each of $R'_1$, $R'_2$ and $R'_3$ represents a hydrogen or halogen atom or a lower alkyl, lower alkoxy or lower alkenyloxy group, provided that $R'_1$, $R'_2$ and $R'_3$ do not represent a hydrogen atom at the same time.

The compound of formula (I) can be prepared, for example, by reacting a compound of the following formula

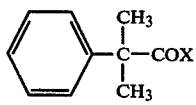 (II)

wherein X represents a halogen atom, especially chlorine or bromine, a lower alkoxy group (e.g., methoxy or ethoxy), or a hydroxyl group, with an aniline derivative of the formula

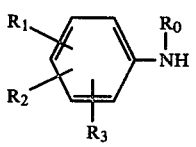 (III)

wherein $R_0$, $R_1$, $R_2$ and $R_3$ are as defined above.

The reaction of the compound of formula (II) with aniline derivative of formula (III) can be carried out in the absence of a solvent. Generally, however, it is carried out in an inert medium. Examples of the inert medium include aromatic hydrocarbons such as benzene, toluene and xylene, ethers such as diethyl ether, tetrahydrofuran, and dioxane, alcohols such as methanol and ethanol, ketones such as acetone and methyl ethyl ketone, and halogenated hydrocarbons such as methylene chloride, chloroform and carbon tetrachloride. Benzene is especially suitable.

The reaction temperature is not critical, and can be varied widely depending upon the type of the starting materials and/or the solvent, etc. Generally, temperatures ranging from about 0° C. to the refluxing temperature of the reactant mixture, preferably about 20° C. to about 40° C., are advantageously used. The reaction pressure is usually atmospheric pressure, but as required, the reaction can be performed under reduced or elevated pressures.

The reaction can be carried out in the presence of general reaction aids. Examples of the reaction aids include alkali metal hydroxides such as sodium hydroxide, alkali metal carbonates such as sodium hydrogen carbonate, organic bases such as pyridine, triethylamine and tripropylamine, dicyclohexylcarbodiimide, phosphorus oxychloride, thionyl chloride, and phosphorus pentachloride. The amount of the reaction aids is desirably one equivalent to the compound of formula (II).

Advantageously, the aniline derivative of formula (III) is used in an amount of about one equivalent to the compound of formula (II).

Under the conditions described above, the reaction ends in about 1 to 3 hours. The recovery and purification of the desired compound of formula (I) from the reaction mixture may be carried out by methods known per se, for example by recrystallization (benzene, toluene, methanol, ethanol, chloroform, hexane, etc. are advantageously used as crystallization solvents), distillation, chromatography, etc.

The compounds of formula (II) used as a starting material in the above reaction, i.e. α,α-dimethylphenylacetic acid, α,α-dimethylphenylacetic acid halides and α,α-dimethylphenylacetic acid esters, are known per se, or can be produced by methods known per se. For example, an α,α-dimethylphenylacetic acid can be produced in a customary manner by reacting α,α-dimethylphenyl acetic acid with a halogenating agent such as thionyl chloride, phosphorus trichloride, phosphorus tribromide or phosphorus pentachloride. An α,α-dimethylphenylacetic acid ester can be produced generally by dehydrocondensing α,α-dimethylphenylacetic acid with an alcohol such as methanol and ethanol.

The production of the compound of formula (I) is illustrated below specifically by working examples.

Example A

A 100 ml. four-necked flask was charged with 50 ml of benzene, 2.02 g of triethylamine and 2.21 g of m-ethylaniline, and with cooling and stirring in water, 3.33 g of α,α-dimethylphenylacetyl chloride was slowly added dropwise. After the addition, a dehydrating tube was attached to the flask, and the mixture in the flask was stirred overnight at room temperature. After the reaction, the reaction solution was washed with water to remove triethylamine hydrochloride. The benzene layer was dried over anhydrous sodium sulfate, and the solvent was distilled off under reduced pressure. Recrystallization of the residue from hexane afforded 3.95 g of α,α-dimethylphenylaceto-m-ethylanilide.

Melting point: 78°–79° C.

IR ($\nu_{max}^{nujol}$ cm⁻¹): 3300 (N-H), 1660 (C=O).

| Elemental analysis for $C_{18}H_{21}NO$: | | | |
|---|---|---|---|
| | C | H | N |
| Calculated (%): | 80.87 | 7.91 | 5.24 |
| Found (%): | 80.86 | 7.93 | 5.24 |

Example B

A 100 ml. four-necked flask was charged with 50 ml of benzene, 1.17 g of N-methylaniline and 1.11 g of triethylamine, and with stirring at room temperature 2 g of α,α-dimethylphenylacetyl chloride was added dropwise. After the addition, the reaction solution was stirred at room temperature for 3 hours. After the reaction, the reaction solution was washed with water to remove triethylamine hydrochloride. The benzene layer was dried over anhydrous sodium sulfate, and the solvent was distilled under reduced pressure. The residue was distilled under reduced pressure to give 1.97 g of α,α-dimethylaceto-N-methylanilide.
Boiling point: 109° C. (1 mmHg).
Refractive index: $n_D^{25} = 1.5511$.
IR ($\nu_{max}^{film}$ cm$^{-1}$): 1640 (C=O).

| Elemental analysis for $C_{17}H_{19}NO$: | | | |
|---|---|---|---|
| | C | H | N |
| Calculated (%): | 80.60 | 7.55 | 5.53 |
| Found (%): | 80.54 | 7.60 | 5.50 |

The compounds shown in Table I below can be produced by the same method as in Example A or B. Table I also gives the compounds obtained in Examples A and B (compounds Nos. 7 and 34).

TABLE 1

| Compound No. | Chemical structure | Appearance | Melting point (°C.) or refractive index ($n_D^{25}$) | Elemental analysis C | H | N | halogen |
|---|---|---|---|---|---|---|---|
| 1 | (structure with two CH₃ groups, C-CO-NH-phenyl) ($C_{16}H_{17}NO$) | White solid | 100–101° C. | 80.31 / 80.29 | 7.15 / 7.18 | 5.85 / 5.84 | — |
| 2 | (structure with CH₃ on anilide ring) ($C_{17}H_{19}NO$) | White solid | 101–102° C. | 80.60 / 80.52 | 7.55 / 7.61 | 5.53 / 5.50 | — |
| 3 | (structure with two CH₃ on anilide ring) ($C_{18}H_{21}NO$) | White solid | 105–106° C. | 80.87 / 80.85 | 7.91 / 7.90 | 5.24 / 5.20 | — |
| 4 | (structure with CH₃ and Cl on anilide ring) ($C_{17}H_{18}NOCl$) | White solid | 130–131° C. | 70.95 / 70.93 | 6.30 / 6.27 | 4.87 / 4.87 | — |
| 5 | (structure with Cl and CH₃ on anilide ring) ($C_{17}H_{18}NOCl$) | White solid | 130.5–131° C. | 70.95 / 70.88 | 6.30 / 6.37 | 4.87 / 4.85 | — |
| 6 | (structure with CH₃ and Cl on anilide ring) ($C_{17}H_{18}NOCl$) | White solid | 88–90° C. | 70.95 / 70.91 | 6.30 / 6.32 | 4.87 / 4.81 | — |

TABLE 1-continued

| Compound No. | Chemical structure | Appearance | Melting point (°C.) or refractive index ($n_D^{25}$) | Elemental analysis C | H | N | halogen |
|---|---|---|---|---|---|---|---|
| 7 | 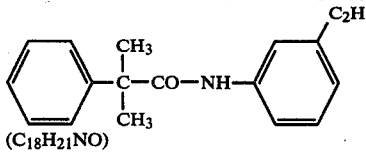 (C₁₈H₂₁NO) 3-C₂H₅ | White solid | 78–79° C. | 80.87 80.86 | 7.91 7.93 | 5.24 5.24 | — — |
| 8 | 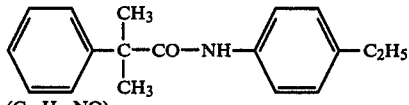 (C₁₈H₂₁NO) 4-C₂H₅ | White solid | 92.5–93.5° C. | 80.87 80.88 | 7.91 7.99 | 5.24 5.20 | — — |
| 9 | 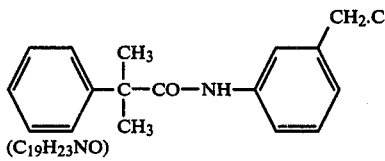 (C₁₉H₂₃NO) 3-CH₂.CH₂.CH₃ | White solid | 52.5–53.5° C. | 81.10 81.20 | 8.23 8.25 | 4.98 4.96 | — — |
| 10 | 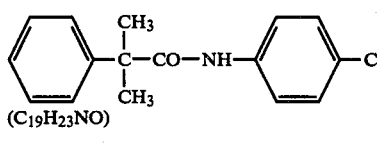 (C₁₉H₂₃NO) 4-CH₂.CH₂.CH₃ | White solid | 71–72° C. | 81.10 81.10 | 8.23 8.23 | 4.98 4.97 | — — |
| 11 | 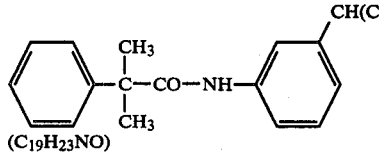 (C₁₉H₂₃NO) 3-CH(CH₃)₂ | White solid | 69–70° C. | 81.10 81.23 | 8.23 8.20 | 4.98 4.90 | — — |
| 12 | 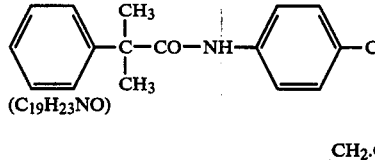 (C₁₉H₂₃NO) 4-CH(CH₃)₂ | White solid | 108–109° C. | 81.10 81.13 | 8.23 8.22 | 4.98 4.96 | — — |
| 13 | 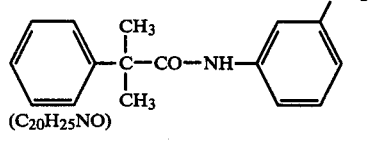 (C₂₀H₂₅NO) 3-CH₂.CH₂.CH₂.CH₃ | White solid | 65–66° C. | 81.32 81.33 | 8.52 8.52 | 4.74 4.70 | — — |
| 14 | 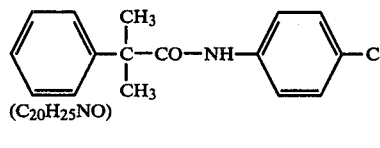 (C₂₀H₂₅NO) 4-CH₂.CH₂.CH₂.CH₃ | White solid | 88–89° C. | 81.32 81.30 | 8.52 8.60 | 4.74 4.70 | — — |
| 15 | 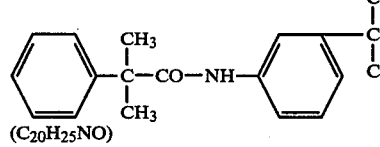 (C₂₀H₂₅NO) 3-C(CH₃)₃ | White solid | 89–90° C. | 81.32 81.31 | 8.52 8.60 | 4.74 4.72 | — — |
| 16 | 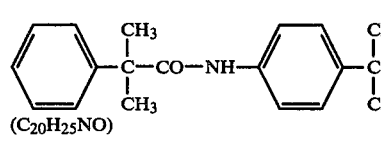 (C₂₀H₂₅NO) 4-C(CH₃)₃ | White solid | 120–121° C. | 81.32 81.33 | 8.52 8.49 | 4.74 4.73 | — — |

TABLE 1-continued

| Compound No. | Chemical structure | Appearance | Melting point (°C.) or refractive index ($n_D^{25}$) | Elemental analysis C | H | N | halogen |
|---|---|---|---|---|---|---|---|
| 17 | 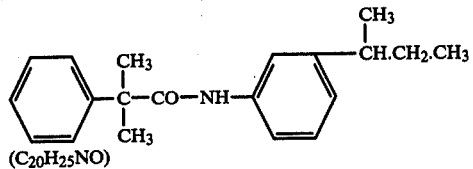 (C₂₀H₂₅NO) | White solid | 51–52° C. | 81.32<br>81.29 | 8.52<br>8.55 | 4.74<br>4.71 | —<br>— |
| 18 | 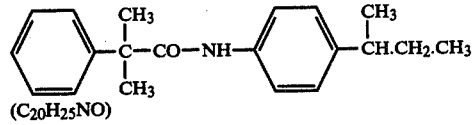 (C₂₀H₂₅NO) | White solid | 69–70° C. | 81.32<br>81.30 | 8.52<br>8.57 | 4.74<br>4.74 | —<br>— |
| 19 | 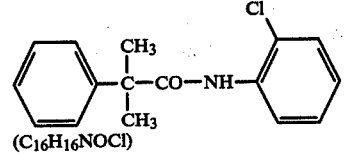 (C₁₆H₁₆NOCl) | White solid | 38–39° C. | 70.20<br>70.18 | 5.89<br>5.90 | 5.12<br>5.10 | 12.95 (Cl)<br>13.00 (Cl) |
| 20 | 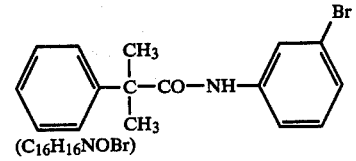 (C₁₆H₁₆NOBr) | White solid | 129–130° C. | 60.39<br>60.30 | 5.06<br>5.12 | 4.40<br>4.36 | 25.11 (Br)<br>25.21 (Br) |
| 21 | 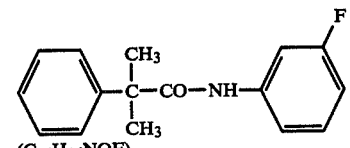 (C₁₆H₁₆NOF) | White solid | 99.5–101° C. | 74.69<br>74.60 | 6.26<br>6.31 | 5.44<br>5.45 | —<br>— |
| 22 | 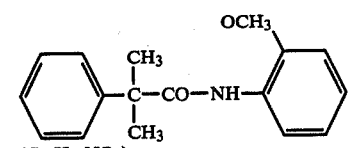 (C₁₇H₁₉NO₂) | Liquid | $n_D^{25}$ 1.5690 | 75.81<br>75.80 | 7.10<br>7.22 | 5.20<br>5.14 | —<br>— |
| 23 | 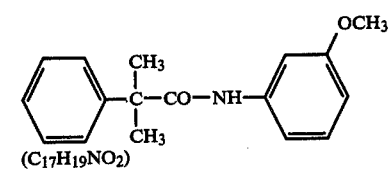 (C₁₇H₁₉NO₂) | White solid | 134–135° C. | 75.81<br>75.78 | 7.10<br>7.11 | 5.20<br>5.20 | —<br>— |
| 24 | 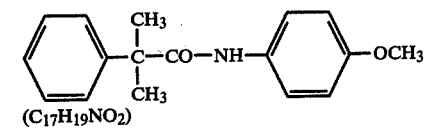 (C₁₇H₁₉NO₂) | White solid | 137–138° C. | 75.81<br>75.77 | 7.10<br>7.13 | 5.20<br>5.18 | —<br>— |
| 25 | 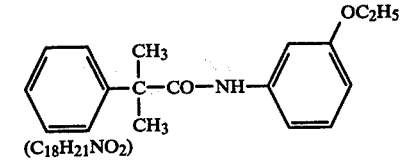 (C₁₈H₂₁NO₂) | White solid | 124–125° C. | 76.30<br>76.23 | 7.46<br>7.48 | 4.94<br>4.96 | —<br>— |

TABLE 1-continued
| Compound No. | Chemical structure | Appearance | Melting point (°C.) or refractive index ($n_D^{25}$) | Elemental analysis C | H | N | halogen |
|---|---|---|---|---|---|---|---|
| 26 | 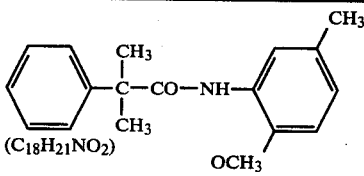 (C₁₈H₂₁NO₂) | White solid | 74–75° C. | 76.30 76.30 | 7.46 7.47 | 4.94 4.95 | — — |
| 27 | 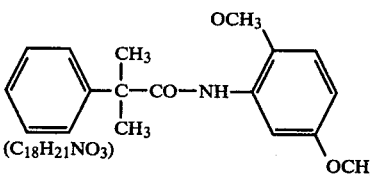 (C₁₈H₂₁NO₃) | Liquid | $n_D^{25}$ 1.5710 | 72.20 72.20 | 7.06 7.08 | 4.68 4.65 | — — |
| 28 | 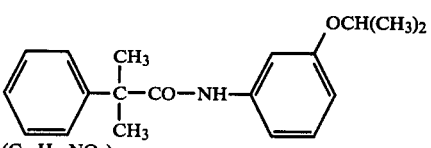 (C₁₉H₂₃NO₂) | White solid | 103.5–104.5° C. | 76.74 76.73 | 7.79 7.80 | 4.71 4.66 | — — |
| 29 | 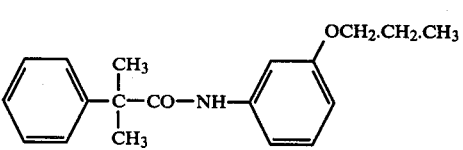 (C₁₉H₂₃NO₂) | White solid | 106–107° C. | 76.74 76.70 | 7.79 7.73 | 4.71 4.70 | — — |
| 30 | 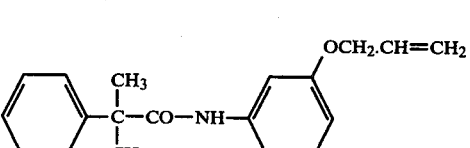 (C₁₉H₂₁NO₂) | White solid | 97.5–98.5° C. | 77.26 77.22 | 7.16 7.20 | 4.74 4.78 | — — |
| 31 | 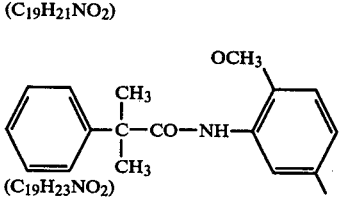 (C₁₉H₂₃NO₂) | White solid | 69.5–70.5° C. | 76.74 76.73 | 7.79 7.75 | 4.71 4.70 | — — |
| 32 | 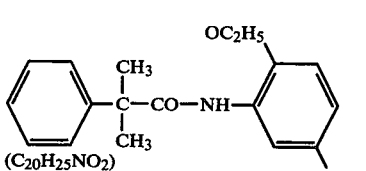 (C₂₀H₂₅NO₂) | White solid | 72.5–73.5° C. | 77.14 77.15 | 8.08 8.07 | 4.50 4.49 | — — |
| 33 | 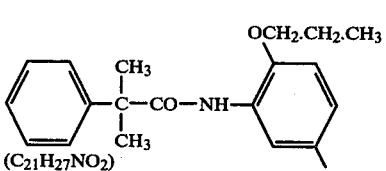 (C₂₁H₂₇NO₂) | Liquid | $n_D^{25}$ 1.5470 | 77.51 77.50 | 8.35 8.34 | 4.30 4.29 | — — |
| 34 | 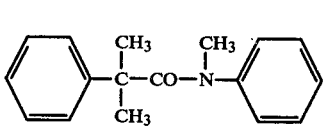 (C₁₇H₁₉NO) | " | $n_D^{25}$ 1.5511 | 80.60 80.54 | 7.55 7.60 | 5.53 5.50 | — — |

TABLE 1-continued

| Compound No. | Chemical structure | Appearance | Melting point (°C.) or refractive index ($n_D^{25}$) | C | H | N | halogen |
|---|---|---|---|---|---|---|---|
| 35 | 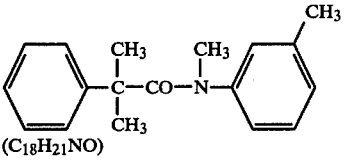 ($C_{18}H_{21}NO$) | White solid | 43–44° C. | 80.87<br>80.82 | 7.91<br>7.93 | 5.24<br>5.20 | —<br>— |
| 36 | 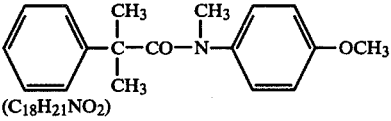 ($C_{18}H_{21}NO_2$) | Liquid | $n_D^{25}$ 1.5592 | 76.30<br>76.10 | 7.46<br>7.50 | 4.94<br>4.92 | —<br>— |
| 37 | 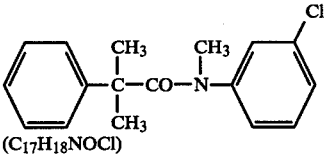 ($C_{17}H_{18}NOCl$) | " | $n_D^{25}$ 1.5726 | 70.95<br>70.94 | 6.30<br>6.35 | 4.87<br>4.90 | 12.32 (Cl)<br>12.44 (Cl) |
| 38 | 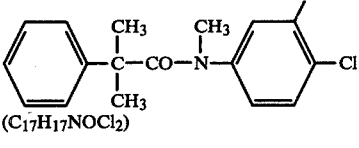 ($C_{17}H_{17}NOCl_2$) | " | $n_D^{25}$ 1.5781 | 63.37<br>63.29 | 5.31<br>5.40 | 4.35<br>4.38 | 22.01 (Cl)<br>22.20 (Cl) |
| 39 | 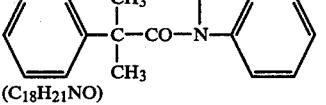 ($C_{18}H_{21}NO$) | " | $n_D^{25}$ 1.5548 | 80.87<br>80.79 | 7.91<br>8.00 | 5.24<br>5.10 | —<br>— |
| 40 | 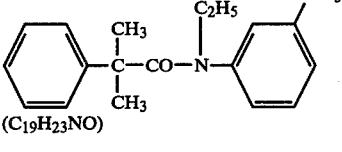 ($C_{19}H_{23}NO$) | " | $n_D^{25}$ 1.5423 | 81.10<br>81.03 | 8.23<br>8.24 | 4.98<br>4.93 | —<br>— |
| 41 | 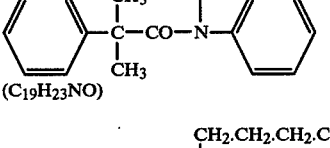 ($C_{19}H_{23}NO$) | " | $n_D^{25}$ 1.5440 | 81.10<br>81.03 | 8.23<br>8.25 | 4.98<br>4.90 | —<br>— |
| 42 | 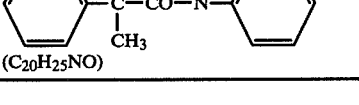 ($C_{20}H_{25}NO$) | " | $n_D^{25}$ 1.5583 | 81.32<br>81.30 | 8.52<br>8.55 | 4.74<br>4.70 | —<br>— |

The compounds of formula (I) provided by this invention have superior herbicidal activities, and are useful as active ingredients of herbicides for controlling various weeds in agricultural crops. Examples of weeds which can be controlled by the compounds of formula (I) are various species of barnyard grass (such as Echinochloa crus-galli Beauv., Echinochloa crus-galli var. oryzicola Ohwi, and Echinochloa crus-galli Subsp. genuina var. echinata Honda), spike-rush (Eleocharis pellucida Presl), sedge sp. (Cyperus hakonensis Saiat), umbrella plant (Cyperus difformis L.), pipewort (Eriocaulon sieboldtianum Sieb), waterwort (Elatine triandra), redstem sp. (Rotala indica Koehne), bulrush (Scirpus juncoides Roxb), redstem sp. (Ammannia multiform Roxb.), false pimpernel (Lindernia pyxidaria L), and slender spikerush (Eleocharis acicularis Roem. et Schalt var. longiseta Svenson). These examples are not limitative, and it should be understood that the compounds of formula (I) exhibit herbicidal effects also against other kinds of weeds.

It has been found that the compounds of formula exhibit marked effects in controlling weeds which occur in fields containing much water, such as a paddy field, rather than those which occur in dry upland fields.

Thus, the compounds of formula (I) exhibit excellent control effects against various species of barnyard grass, especially Echinochloa crus-galli Beauv. which is a very hazardous weed in an aquatic paddy and is considered as one of the five greatest weeds in the world. This weed grows in paddy fields, especially submerged paddy fields, throughout the world. The compounds of formula (I) have the ability to inhibit the germination of the barnyard grass strongly and to prevent its growth in paddy fields.

Moreover, the compounds of formula (I) are very characteristic in that they have excellent selective herbicidal activity which ensures substantial freedom from phytotoxicity to useful agricultural crops such as rice.

Many herbicides have heretofore been suggested for application to paddy fields, and some have come into actual use. Almost none of them, however, have selectivity in physiological herbicidal action between barnyard grass and rice plant. The conventional methods for weed killing in paddy fields are directed to the treatment of paddy fields in the rice growing stage (including the transplanting stage) to control the sprouting of barnyard grass. They are based either on the utilization of the differences in resistance to herbicides between barnyard grass and rice plant according to the differences in their growing stages, or on the principle of chemical adsorption in the upper layer of soil ("artificial selectivity") whereby rice plants are transplanted in such a manner that their roots are located below the herbicide-treated layer, and barnyard grass in the upper layer is controlled while protecting the rice plants from the herbicide.

Barnyard grass is a gramineous weed, as is rice, and they physiologically resemble each other. Hence, controlling of barnyard grass with herbicidal chemicals often causes phytotoxicity to rice plant, and it is extremely difficult to control this weed selectively in paddy fields. Barnyard grass has therefore been considered to be difficult to eradicate in paddy fields, and there has been a strong demand for the advent of herbicides which can selectively control barnyard grass.

The compounds of formula (I) meet this demand of agriculture. They have the excellent property of acting selectively on the seeds and seedlings of barnyard grass to strongly inhibit their germination, but causing no substantial phytotoxicity to rice plant. This property makes the compounds of formula (I) very suitable as active ingredients of herbicides for application to paddy fields.

The superior herbicidal activity of the compounds (I) can be demonstrated by the experimental fact that when N-(3-n-propylphenyl)-$\alpha,\alpha$-dimethylphenylacetamide (compound No. 9) was applied at a rate of 62.5 g per 10 ares to a paddy field where rice plant and barnyard grass were simultaneously sown, the germination of the barnyard grass was completely inhibited, whereas the rice plant showed normal emergence and growth without any phytotoxicity, and that even when the rate of the compound applied was increased to 1,000 g per 10 ares, the rice plant showed normal germination and growth without any phytotoxicity. Thus, the compound of formula (I), when applied in an amount about 20 times as large as the amount required for completely controlling barnyard grass, does not exert any substantial effect on the germination and growth of rice plant.

Such a high selectivity of the compounds in accordance with this invention between barnyard grass and rice plant is ascribable presumably to the specific physiological activities of the compounds against barnyard grass and rice plant. This superior selectivity cannot be expected from the conventional herbicides available for application to paddy fields.

The compound of formula (I) may be applied directly as a herbicide. Generally, however, it is formulated into a herbicidal composition by mixing it with inert liquid or solid carriers or diluents which are commonly employed in herbicide formulations.

In the present invention, any inert liquid or solid agriculturally acceptable carriers or diluents known in the art can be used. Examples of the inert solid carrier or diluent are kaolin, diatomaceous earth, talc bentonite, silica, calcium carbonate and clay materials. Examples of the inert liquid carrier or diluent are water, xylene, toluene, benzene, kerosene, ethyl acetate, methanol, ethano., N,N-dimethyl formamide, dimethyl sulfoxide, and liquefied gases such as tetrafluoroethane.

In addition to the inert liquid or solid carrier or diluent, the herbicidal composition may, as needed, contain nonionic, anionic, cationic or amphoteric surface-active agents such as polyoxyethylene alkyl ethers, polyoxyethylene alkyl aryl ethers, polyoxyethylene fatty acid esters, alkylsulfonate salts, and polyoxyethylene alkylsulfate esters, and/or polymeric compounds such as carboxy methyl cellulose, polyvinyl alcohol and sodium alginate, in usual amounts chosen according to the form of the herbicidal composition.

The herbicidal composition may contain the active compound of formula (I) in an amount of at least 0.5% by weight, preferably 1 to 99% by weight, more preferably 2 to 80% by weight, based on the weight of the composition itself.

The herbicidal composition can be in any conventional forms as a dust, granule, wettable powder, solution, emulsifiable concentrate, or spray according to the method of application. Any methods of formulation known in that art can be used for this purpose. For example, when making a dust, granule or wettable powder, at least one active compound of formula (I) is mixed with at least one inert solid carrier or diluent. The mixture is pulverized and mixed uniformly with a suitable amount of a surface active agent. The solution or emulsifiable concentrate can be prepared by dissolving or dispersing at least one active compound of formula (I) in at least one inert liquid carrier or diluent, followed, if desired, by adding a surface active agent.

Conveniently, the amount of the active compound of formula (I) is 3 to 20% by weight for the dust and granule, 25 to 75% by weight for the wettable powder, and 20 to 50% by weight for the solution and emulsifiable concentrate, all based on the weight of the resulting composition.

The herbicidal composition may further contain agricultural chemicals commonly used in cultivating agricultural crops, such as fungicides, insecticides, nematocides, plant growth controlling agents and fertilizers. Typical examples of the fungicides are Benomyl [methyl 1-(N-butylaminocarbonyl)-1H-benzimidazol-2-yl-carbamate], Hymexazol (5-methyl-3-isoxazolol), Captan [3a,4,7,7a-tetrahydro-N-(trichloromethanesulphenyl)phthalimide], and Zineb [zinc ethylenebis(dithiocarbamate)]. Examples of the insecticides are Disulfoton (O,O-diethyl S-2-ethylthioethyl phosphorodithioate) and Propoxur (2-isopropoxyphenyl methylcarbamate). Examples of the nematocides are Methomyl [S-methyl N-(methylcarbamoyloxy)thioacetamidate] and Alidicarb [2-methyl-2-(methylthio)propionaldehyde O-methylcarbamoyloxime].

It is also possible to incorporate at least one other herbicidally active compound used heretofore in the art into the herbicidal composition of this invention. This frequently brings about a high herbicidal effect against a broad spectrum of weeds. Examples of the other herbicidally active compounds are given below. It should be understood that these examples are not limitative, and other active compounds can be equally incorporated in the herbicidal composition of this invention as required.

Phenoxycarboxylic acid-type herbicides such as 2,4-dichlorophenoxyacetic acid, allyl 2-methyl-4-chlorophenoxyacetate, S-ethyl 2-methyl-4-chlorophenoxyacetate, 2-methyl-4-chlorophenoxyacetic acid (including its esters and salts) and 2-methyl-4-chlorophenoxybutyric acid (including its esters and salts); diphenyl ether-type herbicides such as 3-methyl-4'-nitrodiphenyl ether, 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; organophosphorus-type herbicides such as O-ethyl-O-(2-nitro-5-methylphenyl)N-secondary butyl phosphoroamidothioate, S-(2-methyl-1-piperidylcarbonylmethyl) O,O-di-n-propyldithiophosphate, and O,O-diisopropyl-2-(benzenesulfonamido)ethyldithiophosphate; thiolcarbamate-type herbicides such as S-(4-chlorobenzyl)-N,N-diethylthiolcarbamate, S-benzyl-N-ethyl-N-isobutylthiolcarbamate, S-ethyl-N,N-hexamethylenethiolcarbamate and S-isopropyl-N,N-hexamethylenethiolcarbamate; urea-type herbicides such as 1-(2,2-dimethylbenzyl)-3-(p-tolyl)urea and N-α,α-dimethylbenzyl-α-bromo-t.-butylacetamide; triazine-type herbicides such as 2-methylthio-4,6-bis-ethylamino-1,3,5-triazine, 2-methyl-thio-4,6-bis-isopropylamino-1,3,5-triazine, 2-methylthio-4-ethylamino-6-(1,2-dimethylpropylamino)-1,3,5-triazine and 2-methylthio-4-ethylamino-6-isopropylamino-1,3,5-triazine; amide-type herbicides such as 3,4-dichloropropionanilide, α-(β-naphthoxy)-propionanilide, 2-chloro-2',6'-diethyl-N-(butoxymethyl)acetanilide, 2-chloro-2',6'-diethyl-N-(propoxyethyl)-acetanilide and 2-(α-naphthoxy)-N,N-diethylpropionamide; pyrazol-type herbicides such as 4-(2,4-dichlorobenzoyl)-1,3-dimethyl-5-pyrazolyl-4-toluenesulfonate and 1,3-dimethyl-4-(2,4-dichlorobenzoyl)-5-benzoyl-methoxy-pyrazole; and other herbicides such as 5-t-butyl-3-(2,4-dichloro-5-isopropoxyphenyl)-1,3,4-oxadiazolin-2-one, 3-isopropyl-1H-2,1,3-benzothiaziadin(4)-3H-one-2,2-dioxide, and 2-amino-1,3-chloro-1,4-naphthoquinone.

The herbicidal compositions of this invention containing these other herbicidally active compounds are especially useful for application to paddy fields in the rice growing stage, for example to a paddy field in which transplantation has ended.

The herbicide containing the compound of formula (I) as an active ingredient can be used to control various weeds in areas where agricultural crops are cultivated. In particular, the herbicide of this invention is effective against weeds in wet paddies rather than dry fields, and exhibits a very strong selective herbicidal effect against barnyard grass which accompanies rice plant in paddy fields, such as *Echinochloa crus-galli Beauv.*

Herbicides containing as active ingredients 2,4,6-trichlorophenyl-4'-nitrophenyl ether (MO or CNP), S-(4-chlorobenzyl)-N,N-diethylthiocarbamate (Benthiocarb), 2-chloro-2',6'-diethyl-N-(butoxymethyl)acetanilide (Butachlor), and S-ethyl-N,N-hexamethylenethiocarbamate (Molinate), which now gain widespread acceptance for application to paddy fields, do not show selectivity between barnyard grass and rice plant in the germinating stage, nor are they absolutely safe to transplanted rice plants in the early stage of growth. With these conventional herbicides, the risk of phytotoxicity cannot be avoided in the event of changes in the environmental condition of paddy fields, for example when rice plants are transplanted shallow at the soil surface, the soil is sandy, the water leaks, root growth is abnormal, or the temperature becomes unusually high.

Since the herbicide provided by this invention is based on physiological selectivity, it has the advantage of being applicable to all growing stages of rice plants ranging from the germinating to the growing stage, and being substantially free from phytotoxicity to rice plants by changes in environmental conditions. Thus, it contributes greatly to the cultivation of agricultural crops.

Heretofore, 3',4'-dichloropropionanilide (Propanil) has been used worldwide as an agent having selective activity against barnyard grass in a paddy field. Propanil, however, is an agent suited for foliar application and has no effect of inhibiting germination. In contrast, the herbicide of this invention exhibits far higher selective activity during the emergence of barnyard grass and rice plant than Propanil, and it is no exaggeration to say that the herbicide of this invention is an epoch-making weed killer having no equal among known herbicides of this kind.

In use, the herbicides of this invention containing the active ingredient of formula (I) is applied to the locus to be protected from weeds.

Thus, according to still another aspect of this invention, there is provided a method for controlling weeds in agricultural crops which comprises applying the compound of general formula (I) described hereinbefore to the locus to be protected from the weeds.

The time of application of the compound of formula (I) is not strictly limited, and differs according to the agricultural crops and/or the weeds to be controlled. Generally, in order for the active compound of formula I to exhibit the best herbicidal effect, it is most convenient to apply it just before the weeds to be controlled sprout, or during their germinating stage. It is of course possible to apply it to weeds after emergence, and this brings about some extent of control effect.

There is no particular restriction on the locus to which the active compound of this invention can be applied. It can be applied to various types of agricultural land as is the case with conventional herbicides. It can be best applied however to wet paddies, especially aquatic paddies in the submerged state, and when applied to upland fields of low water content, the active compound of this invention tends to have a somewhat decreased herbicidal effect.

In order for the herbicide of this invention to exhibit its herbicidal effect most, it is applied to a field in a submerged condition before or during the germination of weeds.

The active compounds of formula (I) of this invention exhibit herbicidal effects against the various weeds described hereinabove, but have excellent effects of inhibiting germination of various kinds of barnyard grass, especially Echinochloa crus-galli Beauv. which accompany rice plants, without any substantial toxicity to rice plant. Thus, the active compounds formula (I) can be effectively applied to control barnyard grass selectively and protect rice plants therefrom.

The rate of application of the active compound of formula (I) is not critical, and can be varied widely according to the type of the active compound, the time of application, the procedure of application, etc. Advantageously, it is generally at least 20 g, preferably 30 g to 1000 g, more preferably 50 g to 500 g, per 10 ares.

The method of application may be any conventional method. For example, the herbicidal composition of this invention may be sprayed onto the locus to be protected from weeds from above the ground or from the air. Or it may be sprayed together with the seeds of an agricultural crop at the time of seeding the crop.

Furthermore, according to the present invention, seeds of a crop may be dipped prior to sowing in an aqueous liquid containing the active compound of formula (I) to control the germination of weed seeds that may be present in admixture with the crop seeds.

The active compounds of formula (I) have little toxicity to useful agricultural crops and low mammalian toxicity, and therefore are very suitable as herbicides.

The following Examples further illustrate the formulation of the herbicides provided by the present invention, and their selective herbicidal activities.

In these Examples, all parts and percentages are by weight. The numbers of the compounds refer to those given in Table 1.

Example 1

Dust:

Three parts of compound No. 7, 0.3 part of isopropyl acid phosphate, 66.7 parts of clay, and 30 parts of talc were mixed and pulverized to form a dust.

Example 2

Wettable powder:

Fifty parts of the compound No. 1, 45 parts of diatomaceous earth, 2 parts of polyvinyl alcohol and 3 parts of sodium dodecylbenzenesulfonate were mixed and pulverized to form a wettable powder.

Example 3

Emulsifiable concentrate:

Thirty parts of compound No. 23, 60 parts of xylene and 10 parts of polyoxyethylene alkyl aryl ether were mixed with stirring to form an emulsifiable concentrate.

Example 4

Granules:

Five parts of compound No. 34, 70 parts of bentonite, 20 parts of talc, 4 parts of sodium lignin-sulfonate and 1 part of sodium laurate were mixed and pulverized. A suitable amount of water was added to the pulverized mixture and they were kneaded. The mixture was granulated by an extrusion-type granulator, then dried with air by a fluidized drying device, and then sieved to a definite particle size to form granules.

Example 5

Granules:

Bentonite (25 parts), 71.7 parts of talc, 2 parts of sodium ligninsulfonate, 0.5 part of sodium alkylbenzenesulfonate and 0.8 part of sodium bicarbonate were mixed and pulverized. A suitable amount of water was added to the pulverized mixture, and they were kneaded. The mixture was granulated by an extrusion-type granulator, dried with air by a fluidized drying device, and sieved to a definite particle size to form granules.

Then, 95 parts of the granules were impregnated with 5 parts of compound No. 27 to form granules.

Example 6

Soil from a rice paddy were filled in pots (1/10,000 are). Seeds of barnyard grass and umbrella plant were sown in the surface layer, and tubers of water nutgrass were planted. Water was filled in the pots to provide a water depth of 3 cm. Before the germination of these weeds, the watered soil was treated with a predetermined amount of a wettable powder prepared in accordance with Example 2, and the herbicidal efficacy of the chemical was observed three weeks after the treatment. The herbicidal effect was evaluated on the following standards. The results are shown in Table 2.

TABLE 2

| Compound No. | Amount of active Component (g/a) | Herbicidal effect | | |
|---|---|---|---|---|
| | | Barnyard grass | Umbrella plant | Water-nutgrass |
| 1 | 25.0 | 5 | 5 | 5 |
| | 12.5 | 5 | 4 | 4 |
| 2 | 25.0 | 5 | 5 | 5 |
| | 12.5 | 5 | 5 | 4 |
| 3 | 25.0 | 5 | 5 | 5 |
| | 12.5 | 4 | 4 | 5 |
| 4 | 25.0 | 4 | 4 | 4 |
| | 12.5 | 4 | 4 | 3 |
| 5 | 25.0 | 5 | 5 | 4 |
| | 12.5 | 4 | 4 | 4 |
| 6 | 25.0 | 4 | 4 | 3 |
| | 12.5 | 4 | 4 | 3 |
| 7 | 25.0 | 5 | 5 | 5 |
| | 12.5 | 5 | 5 | 5 |
| 8 | 25.0 | 5 | 5 | 5 |
| | 12.5 | 4 | 4 | 5 |
| 9 | 25.0 | 5 | 5 | 5 |
| | 12.5 | 5 | 5 | 5 |
| 10 | 25.0 | 5 | 5 | 5 |
| | 12.5 | 5 | 4 | 5 |
| 11 | 25.0 | 5 | 5 | 5 |
| | 12.5 | 5 | 5 | 4 |
| 12 | 25.0 | 5 | 5 | 5 |
| | 12.5 | 5 | 4 | 4 |
| 13 | 25.0 | 5 | 5 | 4 |
| | 12.5 | 5 | 5 | 4 |
| 14 | 25.0 | 5 | 4 | 4 |
| | 12.5 | 4 | 4 | 3 |
| 15 | 25.0 | 5 | 5 | 4 |
| | 12.5 | 5 | 4 | 4 |
| 16 | 25.0 | 5 | 4 | 3 |
| | 12.5 | 4 | 4 | 3 |
| 17 | 25.0 | 5 | 5 | 4 |
| | 12.5 | 5 | 4 | 4 |
| 18 | 25.0 | 5 | 4 | 4 |
| | 12.5 | 4 | 4 | 3 |
| 19 | 25.0 | 5 | 4 | 4 |
| | 12.5 | 4 | 3 | 3 |
| 20 | 25.0 | 5 | 3 | 3 |
| | 12.5 | 5 | 2 | 2 |
| 21 | 25.0 | 5 | 3 | 5 |
| | 12.5 | 4 | 3 | 3 |
| 22 | 25.0 | 5 | 3 | 3 |
| | 12.5 | 3 | 2 | 2 |
| 23 | 25.0 | 5 | 4 | 4 |
| | 12.5 | 5 | 3 | 3 |
| 24 | 25.0 | 4 | 4 | 5 |

TABLE 2-continued

| Compound No. | Amount of active Component (g/a) | Herbicidal effect Barnyard grass | Umbrella plant | Water-nutgrass |
|---|---|---|---|---|
|  | 12.5 | 4 | 3 | 3 |
| 25 | 25.0 | 4 | 2 | 2 |
|  | 12.5 | 3 | 0 | 1 |
| 26 | 25.0 | 5 | 3 | 4 |
|  | 12.5 | 4 | 3 | 3 |
| 27 | 25.0 | 5 | 2 | 4 |
|  | 12.5 | 4 | 2 | 3 |
| 28 | 25.0 | 5 | 3 | 3 |
|  | 12.5 | 5 | 2 | 2 |
| 29 | 25.0 | 5 | 4 | 3 |
|  | 12.5 | 5 | 3 | 3 |
| 30 | 25.0 | 3 | 3 | 3 |
|  | 12.5 | 3 | 3 | 1 |
| 31 | 25.0 | 5 | 5 | 5 |
|  | 12.5 | 5 | 5 | 4 |
| 32 | 25.0 | 5 | 5 | 4 |
|  | 12.5 | 4 | 5 | 4 |
| 33 | 25.0 | 4 | 5 | 4 |
|  | 12.5 | 4 | 4 | 4 |
| 34 | 25.0 | 5 | 4 | 4 |
|  | 12.5 | 5 | 3 | 3 |
| 35 | 25.0 | 2 | 4 | 5 |
|  | 12.5 | 2 | 4 | 4 |
| 36 | 25.0 | 2 | 2 | 3 |
|  | 12.5 | 2 | 2 | 2 |
| 37 | 25.0 | 5 | 3 | 4 |
|  | 12.5 | 4 | 2 | 3 |
| 38 | 25.0 | 4 | 4 | 4 |
|  | 12.5 | 4 | 3 | 4 |
| 39 | 25.0 | 4 | 2 | 3 |
|  | 12.5 | 3 | 2 | 3 |
| 40 | 25.0 | 3 | 2 | 3 |
|  | 12.5 | 2 | 2 | 1 |
| 41 | 25.0 | 3 | 2 | 4 |
|  | 12.5 | 1 | 2 | 3 |
| 42 | 25.0 | 3 | 0 | 2 |
|  | 12.5 | 1 | 0 | 0 |
| Benthiocarb | 25.0 | 4 | 4 | 2 |
|  | 12.5 | 3 | 3 | 2 |
| Molinate | 25.0 | 3 | 3 | 3 |
|  | 12.5 | 2 | 2 | 1 |
| Untreated | — | 0 | 0 | 0 |

| Index | Herbicidal effect |
|---|---|
| 5 | Withered |
| 4 | 80-99% control |
| 3 | 60-79% control |
| 2 | 40-59% control |
| 1 | 20-39% control |
| 0 | No control |

Example 7

Soil from a rice paddy was filled in pots (1/5,000 are). Seeds of barnyard grass, umbrella plant and bulrush were sown, and tubers of water nutgrass were planted. Water was filled in the pots to provide a water depth of 3 cm. Five days after the emergence of the weeds, the watered soil was treated with a predetermined amount of granules prepared in accordance with Example 5. Three weeks after the treatment, the degree of phytotoxicity to rice plants transplanted or directly sown and grown and the herbicidal effect of the chemical against the weeds were observed. The results are shown in Table 3.

The herbicidal effect was evaluated on the standards given in Example 6. The degree of phytotoxicity to rice was evaluated on the following standard.

TABLE 3

| Compound No. | Amount of the active ingredient (g/a) | Herbicidal effect Barnyard grass | Umbrella plant | Water nutgrass | Bulrush | Phytotoxicity to rice |
|---|---|---|---|---|---|---|
| 1 | 50.0 | 5 | 4 | 5 | 4 | — |
|  | 25.0 | 5 | 4 | 5 | 4 | — |
|  | 12.5 | 5 | 3 | 4 | 3 | — |
| 2 | 50.0 | 5 | 5 | 5 | 5 | — |
|  | 25.0 | 5 | 5 | 5 | 5 | — |
|  | 12.5 | 5 | 5 | 4 | 4 | — |
| 3 | 50.0 | 5 | 5 | 5 | 5 | — |
|  | 25.0 | 5 | 5 | 5 | 5 | — |
|  | 12.5 | 4 | 4 | 4 | 3 | — |
| 4 | 50.0 | 5 | 5 | 4 | 4 | — |
|  | 25.0 | 4 | 4 | 4 | 4 | — |
|  | 12.5 | 4 | 4 | 3 | 3 | — |
| 5 | 50.0 | 5 | 5 | 5 | 5 | — |
|  | 25.0 | 5 | 5 | 4 | 4 | — |
|  | 12.5 | 4 | 4 | 4 | 3 | — |
| 6 | 50.0 | 4 | 4 | 4 | 4 | — |
|  | 25.0 | 4 | 4 | 3 | 3 | — |
|  | 12.5 | 4 | 4 | 3 | 3 | — |
| 7 | 50.0 | 5 | 5 | 5 | 5 | — |
|  | 25.0 | 5 | 5 | 5 | 5 | — |
|  | 12.5 | 5 | 5 | 5 | 4 | — |
| 8 | 50.0 | 5 | 5 | 5 | 5 | — |
|  | 25.0 | 5 | 5 | 5 | 5 | — |
|  | 12.5 | 4 | 4 | 5 | 4 | — |
| 9 | 50.0 | 5 | 5 | 5 | 5 | — |
|  | 25.0 | 5 | 5 | 5 | 4 | — |
|  | 12.5 | 5 | 5 | 5 | 4 | — |
| 10 | 50.0 | 5 | 5 | 5 | 5 | — |
|  | 25.0 | 5 | 5 | 5 | 4 | — |
|  | 12.5 | 5 | 4 | 5 | 4 | — |
| 11 | 50.0 | 5 | 5 | 5 | 5 | — |
|  | 25.0 | 5 | 5 | 5 | 4 | — |
|  | 12.5 | 5 | 5 | 4 | 3 | — |
| 12 | 50.0 | 5 | 5 | 5 | 4 | — |
|  | 25.0 | 5 | 5 | 5 | 4 | — |
|  | 12.5 | 5 | 4 | 4 | 3 | — |
| 13 | 50.0 | 5 | 5 | 5 | 5 | — |
|  | 25.0 | 5 | 5 | 4 | 4 | — |
|  | 12.5 | 5 | 4 | 4 | 3 | — |
| 14 | 50.0 | 5 | 4 | 4 | 4 | — |
|  | 25.0 | 5 | 3 | 4 | 3 | — |
|  | 12.5 | 4 | 3 | 3 | 3 | — |
| 15 | 50.0 | 5 | 5 | 4 | 4 | — |
|  | 25.0 | 5 | 5 | 4 | 3 | — |
|  | 12.5 | 5 | 4 | 4 | 3 | — |
| 16 | 50.0 | 5 | 4 | 4 | 2 | — |
|  | 25.0 | 5 | 4 | 3 | 1 | — |
|  | 12.5 | 4 | 3 | 3 | 0 | — |
| 17 | 50.0 | 5 | 5 | 5 | 4 | — |
|  | 25.0 | 5 | 5 | 4 | 3 | — |
|  | 12.5 | 5 | 4 | 4 | 3 | — |
| 18 | 50.0 | 5 | 4 | 4 | 3 | — |
|  | 25.0 | 4 | 3 | 4 | 2 | — |
|  | 12.5 | 4 | 3 | 3 | 1 | — |
| 19 | 50.0 | 5 | 4 | 5 | 5 | — |
|  | 25.0 | 5 | 4 | 4 | 4 | — |
|  | 12.5 | 4 | 3 | 3 | 3 | — |
| 20 | 50.0 | 5 | 4 | 3 | 3 | — |
|  | 25.0 | 5 | 3 | 3 | 3 | — |
|  | 12.5 | 4 | 2 | 2 | 2 | — |
| 21 | 50.0 | 5 | 5 | 5 | 5 | — |
|  | 25.0 | 5 | 3 | 5 | 2 | — |
|  | 12.5 | 4 | 3 | 3 | 0 | — |
| 22 | 50.0 | 5 | 4 | 4 | 3 | — |
|  | 25.0 | 5 | 3 | 3 | 3 | — |
|  | 12.5 | 3 | 2 | 2 | 2 | — |
| 23 | 50.0 | 5 | 5 | 4 | 2 | — |
|  | 25.0 | 5 | 4 | 4 | 2 | — |
|  | 12.5 | 5 | 3 | 3 | 1 | — |
| 24 | 50.0 | 5 | 4 | 5 | 4 | — |
|  | 25.0 | 4 | 4 | 5 | 3 | — |
|  | 12.5 | 4 | 3 | 3 | 2 | — |
| 25 | 50.0 | 4 | 3 | 3 | 2 | — |
|  | 25.0 | 4 | 2 | 2 | 2 | — |
|  | 12.5 | 3 | 0 | 1 | 1 | — |
| 26 | 50.0 | 5 | 4 | 4 | 4 | — |
|  | 25.0 | 5 | 3 | 4 | 3 | — |

TABLE 3-continued

| Compound No. | Amount of the active ingredient (g/a) | Herbicidal effect ||||  Phytotoxicity to rice |
|---|---|---|---|---|---|---|
| | | Barnyard grass | Umbrella plant | Water nut-grass | Bulrush | |
| | 12.5 | 4 | 3 | 3 | 2 | — |
| 27 | 50.0 | 5 | 3 | 5 | 3 | — |
| | 25.0 | 5 | 2 | 4 | 3 | — |
| | 12.5 | 4 | 2 | 3 | 1 | — |
| 28 | 50.0 | 5 | 3 | 3 | 2 | — |
| | 25.0 | 5 | 3 | 3 | 2 | — |
| | 12.5 | 5 | 2 | 2 | 1 | — |
| 29 | 50.0 | 5 | 4 | 4 | 3 | — |
| | 25.0 | 5 | 4 | 3 | 3 | — |
| | 12.5 | 5 | 3 | 3 | 2 | — |
| 30 | 50.0 | 4 | 4 | 5 | 3 | — |
| | 25.0 | 3 | 3 | 3 | 2 | — |
| | 12.5 | 3 | 3 | 1 | 0 | — |
| 31 | 50.0 | 5 | 5 | 5 | 5 | — |
| | 25.0 | 5 | 5 | 5 | 5 | — |
| | 12.5 | 5 | 5 | 4 | 4 | — |
| 32 | 50.0 | 5 | 5 | 5 | 5 | — |
| | 25.0 | 5 | 5 | 4 | 4 | — |
| | 12.5 | 4 | 5 | 4 | 3 | — |
| 33 | 50.0 | 5 | 5 | 4 | 4 | — |
| | 25.0 | 4 | 5 | 4 | 3 | — |
| | 12.5 | 4 | 4 | 4 | 3 | — |
| 34 | 50.0 | 5 | 5 | 4 | 4 | — |
| | 25.0 | 5 | 4 | 4 | 4 | — |
| | 12.5 | 5 | 3 | 3 | 2 | — |
| 35 | 50.0 | 4 | 5 | 5 | 5 | — |
| | 25.0 | 2 | 4 | 5 | 5 | — |
| | 12.5 | 2 | 4 | 4 | 3 | — |
| 36 | 50.0 | 3 | 3 | 4 | 1 | — |
| | 25.0 | 2 | 3 | 3 | 0 | — |
| | 12.5 | 2 | 2 | 2 | 0 | — |
| 37 | 50.0 | 5 | 4 | 5 | 2 | — |
| | 25.0 | 5 | 3 | 4 | 1 | — |
| | 12.5 | 4 | 2 | 3 | 0 | — |
| 38 | 50.0 | 5 | 5 | 5 | 4 | — |
| | 25.0 | 4 | 4 | 4 | 3 | — |
| | 12.5 | 4 | 3 | 4 | 2 | — |
| 39 | 50.0 | 5 | 3 | 4 | 2 | — |
| | 25.0 | 4 | 2 | 3 | 0 | — |
| | 12.5 | 3 | 2 | 2 | 0 | — |
| 40 | 50.0 | 4 | 3 | 3 | 2 | — |
| | 25.0 | 3 | 2 | 3 | 0 | — |
| | 12.5 | 2 | 2 | 1 | 0 | — |
| 41 | 50.0 | 4 | 3 | 5 | 2 | — |
| | 25.0 | 3 | 2 | 4 | 0 | — |
| | 12.5 | 1 | 2 | 3 | 0 | — |
| 42 | 50.0 | 4 | 1 | 2 | 2 | — |
| | 25.0 | 3 | 0 | 2 | 0 | — |
| | 12.5 | 1 | 0 | 0 | 0 | — |
| Benthiocarb | 50.0 | 5 | 4 | 3 | 3 | ± |
| | 25.0 | 4 | 4 | 2 | 2 | — |
| | 12.5 | 3 | 3 | 2 | 1 | — |
| Molinate | 50.0 | 5 | 4 | 3 | 3 | ± |
| | 25.0 | 3 | 3 | 3 | 2 | — |
| | 12.5 | 2 | 2 | 1 | 1 | — |
| Untreated | — | 0 | 0 | 0 | 0 | — |

—: no injury
±: slight injury
+: small injury
++: medium injury
+++: great injury

What we claim is:

1. A herbicidal composition comprising a herbicidally effective amount of a compound of the formula

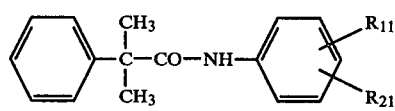

wherein $R_{11}$ and $R_{21}$ each represents hydrogen, methyl, ethyl, propyl, isopropyl or methoxy provided that $R_{11}$ and $R_{21}$ do not both represent hydrogen at the same time, as an active ingredient and an inert liquid or solid carrier or diluent.

2. A composition of claim 1 wherein the active ingredient is a compound of the formula

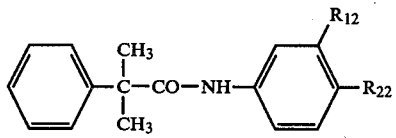

wherein $R_{12}$ and $R_{22}$ each represents hydrogen, methyl, ethyl, propyl or isopropyl, provided that $R_{12}$ and $R_{22}$ do not both represent hydrogen at the same time.

3. A composition of claim 1 wherein the active ingredient is a compound of the formula

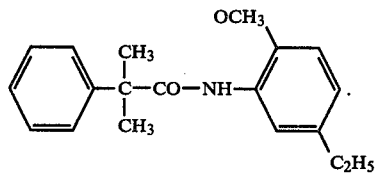

4. A composition of claim 1 wherein the active ingredient is a compound of the formula

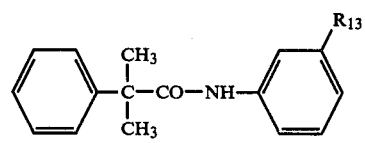

wherein $R_{13}$ represents methyl, ethyl, propyl or isopropyl.

5. A composition of claim 1 wherein the amount of the compound of the formula set forth is at least 0.5% by weight based on the weight of the composition.

6. A composition of claim 1 wherein the amount of the compound of the formula set forth is 1 to 99% by weight based on the weight of the composition.

7. A composition of claim 1 which is in the form of a dust, granule, wettable powder, solution, or emulsifiable concentrate.

8. A method for controlling weeds in agricultural crops which comprises applying a herbicidally effective amount of the formula

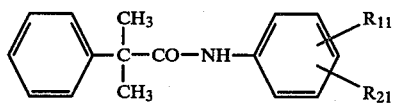

wherein $R_{11}$ and $R_{21}$ each represents hydrogen, methyl, ethyl, propyl, isopropyl or methoxy, provided that $R_{11}$ and $R_{21}$ do not both represent hydrogen at the same time, to the locus to be protected from the weeds.

9. A method of claim 8 wherein the compound of the formula set forth is applied before or during the germination of the weeds.

10. A method of claim 8 wherein the crop is a rice plant.

11. A method of claim 8 wherein the locus is a paddy field.

12. A method of claim 8 wherein the weeds are barnyard grass, umbrella plant, water nutgrass and bulrush.

13. A method of claim 8 wherein the amount of the compound of the formula set forth applied is at least 20 g/10 ares.

14. A method of claim 8 wherein the amount of the compound of the formula set forth applied is 30 to 1000 g/10 ares.

15. A compound of the formula

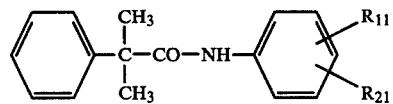

wherein $R_{11}$ and $R_{21}$ each represents hydrogen, methyl, ethyl, propyl, isopropyl or methoxy provided that $R_{11}$ and $R_{21}$ do not both represent hydrogen at the same time.

* * * * *